United States Patent [19]

Gottlieb

[11] 4,363,818

[45] Dec. 14, 1982

[54] METHOD FOR RELIEF OF BURNING, ITCHING, AND PAIN OF CUTANEOUS AND MUCOSAL SURFACES

[76] Inventor: Sheldon K. Gottlieb, 8708 Wandering Trail Dr., Potomac, Md. 20854

[21] Appl. No.: 207,738

[22] Filed: Nov. 17, 1980

Related U.S. Application Data

[63] Continuation-in-part of Ser. No. 126,997, Mar. 3, 1980, abandoned, which is a continuation-in-part of Ser. No. 857,526, Dec. 5, 1977, Pat. No. 4,167,945, which is a continuation-in-part of Ser. No. 764,229, Jan. 31, 1977, Pat. No. 4,061,731, which is a continuation-in-part of Ser. No. 576,858, Jun. 4, 1975, Pat. No. 4,006,220.

[51] Int. Cl.$^3$ ............................................. A61K 31/195
[52] U.S. Cl. ............................. 424/319; 424/DIG. 13
[58] Field of Search ........................ 424/319, DIG. 13

[56] References Cited

U.S. PATENT DOCUMENTS

| | | | |
|---|---|---|---|
| 4,006,220 | 2/1977 | Gottlieb | 424/101 |
| 4,061,731 | 12/1977 | Gottlieb | 424/101 |
| 4,167,945 | 9/1979 | Gottlieb | 424/101 X |

OTHER PUBLICATIONS

Reiss, Brit. J. Derm., vol. 85, p. 76 (1971).
Reiss et al., Dermatologica, vol. 146, pp. 357–360 (1973).
Chem. Abstr. entries 18240$^m$; 97159$^t$; 108358$^k$, (1971).
Chem. Abstr. entry 94779$^e$ (1972).

*Primary Examiner*—Leonard Schenkman
*Attorney, Agent, or Firm*—Schwartz & Weinrieb

[57] ABSTRACT

A method for the drying and diminution of cutaneous and mucosal lesions and the relief of the sensations of burning, pain and itching of cutaneous and mucosal surfaces is discussed. The process comprises the step of topically applying to the situs of the condition being treated, a composition consisting essentially of (A) a compound selected from the group consisting of: (1) aminocaproic acid, (2) a compound of the formula $4NH_2CH_2(CH_2)_4COOH \cdot CaX_2$ wherein X is chloride or bromide, or (3) mixtures thereof, and (B) an inert, pharmaceutically acceptable carrier.

3 Claims, No Drawings

METHOD FOR RELIEF OF BURNING, ITCHING, AND PAIN OF CUTANEOUS AND MUCOSAL SURFACES

CROSS-REFERENCE TO RELATED APPLICATIONS

This application is a continuation-in-part application of my copending application, Ser. No. 126,997, filed Mar. 3, 1980 now abandoned, said application being a continuation-in-part application of my copending application, Ser. No. 857,526, filed Dec. 5, 1977, now U.S. Patent No. 4,167,945, said application being a continuation-in-part of my copending application Ser. No. 764,229, filed Jan. 31, 1977, now U.S. Pat. No. 4,061,731, said application being a continuation-in-part application of my copending application Ser. No. 576,858, filed June 4, 1975, now U.S. Pat. No. 4,006,220.

BACKGROUND OF THE INVENTION

Epsilon-aminocaproic acid and structurally related compounds have long been recognized for their antifibrinolytic properties and for treatment of acute bleeding syndromes. These compounds are administered either intravenously or orally. There is no mention of topical administration of these compounds in the clinical literature.

In addition to its use as an inhibitor of fibrinolysis, epsilon-aminocaproic acid has been previously reported as exhibiting anti-inflammatory properties, when administered orally. See Reiss, "The Therapeutic Effect of Epsilon-Aminocaproic Acid with Special Reference to Atopic Dermatitis," British Journal of Dermatology, Vol. 85, Page 76 (1971). According to Reiss et al, "The Therapeutic Effect of $\epsilon$-Aminocaproic Acid on Anetoderma Jadassohn," *Dermatologica,* Vol. 146, pp. 357–60 (1973), epsilon-aminocaproic acid can be administered orally for the treatment of anetoderma of Jadassohn.

OBJECTS OF THE PRESENT INVENTION

It is a primary object of the present invention to provide a new and efficient method for the drying and diminution of cutaneous and mucosal lesions including, for example, papulonodular, vesiculobullous and erosive-type lesions.

It is a further object of the present invention to provide a method for the relief of the sensations of burning, pain and/or itching of cutaneous and mucosal surfaces which may or may not accompany the aforementioned lesions.

BRIEF SUMMARY OF THE INVENTION

Briefly, the present invention relates to the drying and diminution of cutaneous and mucosal lesions which comprise the step of topically applying to the situs of the lesion(s), a composition consisting essentially of: (A) a compound selected from the group consisting of: (1) aminocaproic acid, (2) a compound of the formula $4NH_2CH_2(CH_2)_4COOH \cdot CaX_2$ wherein X is chloride or bromide, or (3) mixtures thereof, and (B) a pharmaceutically acceptable carrier.

The present invention also relates to the relief of the sensations of burning, pain and/or itching of cutaneous and mucosal surfaces which comprises the step of applying the composition to the situs of the condition wherein the active compound is applied in an amount effective to relieve the condition being treated.

DETAILED DESCRIPTION OF THE INVENTION

The term aminocaproic acid, as used in this specification, is intended to include the various forms of aminocaproic acid as well as epsilon-aminocaproic acid which is particularly preferred for the process of the present invention.

According to one embodiment of the present invention, the process of this invention is effectively used for drying and diminution of one or more cutaneous or mucosal surface lesions, which may be of the papulonodular, vesiculobullous or erosive-type, provided that an effective amount of the pharmacologically active ingredient is applied to the lesions in an amount sufficient to cause the drying and diminution of the lesions. By effective amount, it is intended that between about 0.025 and 0.075 grams of said pharmacologically active ingredient be applied to a surface area generally between about 3 $mm^2$ and 6.45 $cm^2$. Thus, from 0.1 to 0.6 ml, and preferably 0.2 ml of a composition comprising between about 0.25 and 0.75 grams of the pharmacologically active compound, the balance being the inert, pharmaceutically acceptable carrier, is applied to a surface area of between about 3 $mm^2$ and 6.45 $cm^2$ to effectively control the aforementioned condition with proportionally greater amounts being employed for larger or smaller surface areas.

It is understood that the lesions being treated in accordance with this invention are usually present without associated edema. Edema generally refers to the accumulation of tissue fluids which may arise from several causes, e.g., congestive heart failure, nephritis, varicose veins, cirrhosis, and allergic phenomena. Edema is generally a condition existing beneath a cutaneous or mucosal surface, whereas the lesions being treated in accordance with this invention generally exist on said cutaneous or mucosal surfaces.

In addition, the effective amounts of the active ingredient as well as the amount of the composition used for the relief of the sensation of burning, pain and/or itching which may or may not accompany papulonodular, vesiculo-bullous or erosive-type lesions (erosions, minor lacerations, abrasions, fissures and ulcerations) is an amount effective to diminish said burning, pain and/or itching of the cutaneous or mucosal surface at the situs of such condition. This process may also be used for the relief of the sensation of burning, pain and/or itching not associated with the aforementioned cutaneous or mucosal lesions, but due to heat burn, sunburn, water burn, chemical burn, and contact dermatitis.

It is also noted that erythema of cutaneous and/or mucosal surfaces may, or may not be present when an individual experiences the sensation of burning, pain and/or itching of said surfaces. If erythema is present with the burning, pain and/or itching sensations, the process of this invention tends to diminish the erythema while relieving the burning, pain and/or itching sensation. The amount of the composition used is generally between 0.1 and 0.6 ml of the composition for a surface area between about 3 $mm^2$ and 6.45 $cm^2$ with proportionally greater amounts being employed for larger or smaller surface areas.

The term "diminution," as used in this specification, refers to the reduction in size and/or flattening of a lesion, or reduction in degree of sensation, being treated in accordance with this invention.

Carrier materials suitable for use in the instant process include those well-known for use in the medical art as bases for ointments, solutions, lotions, powders, salves, creams, aerosols, gels, and the like. Suitable carriers include, for example, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in medicinal compositions. Exemplary carriers herein include alcohols, including both monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, and stearoyl diacetin. Oil-in-water emulsions such as cold cream bases can also be used.

Preferably, the carrier herein is the pharmaceutically acceptable liquid alcohol containing from about 2 to about 6 carbon atoms. Mixtures comprising from about 0% to 80% by weight of water and about 20% to 100% by weight of said $C_2$ to $C_6$ alcohols are also suitable. Suitable alcohols herein include ethanol, isopropanol, hexanol, and the like. Especially preferred carriers herein are water-ethanol (ethyl alcohol) mixtures at a weight ratio of about 1:20 to 5:1. Ethanol containing from about 5% to about 50% by weight of water, especially 40:60 volume (i.e., 33.35% by weight) ethanol-water, is preferred as the carrier.

The compositions herein can also include various agents and ingredients commonly employed in dermatological ointments and lotions. For example, thickening agents, such as carboxymethylcellulose, coloring agents and the like can be present in the compositions to provide a more pleasing aesthetic aspect.

The term "pharmaceutically acceptable carrier," as used herein, is meant to include any liquid, gel, solvent, liquid diluent, fluid ointment base, fluid suppository base and the like, which is suitable for use in contact with living animal tissue without any untoward physiological response and which does not interact with the other components of the compositions in a deleterious manner and which can be used to establish the compositions herein in their preferred liquid form.

It is understood that the process of the present invention also relates to the diminution of erythema sometimes accompanying papulonodular, vesiculobullous, or erosive-type lesions when the active ingredient is used in an amount effective to cause the drying and diminution of these lesions. It is also understood that the treatable erythema need not be associated with the lesions being treated in accordance with this invention.

It is understood that the processes of this invention are to be used for the treatment of the discussed conditions in both animals and humans.

EXAMPLE

A composition of the following ingredients is useful for the relief of burning, itching and pain associated with a small cutaneous laceration (about 5 cm long and 1 mm wide):

| Epsilon-aminocaproic acid | 5 gms |
|---|---|
| Water | 20 ml (approximate) |
| Hydrochloric acid | To adjust pH to about 6.8 |
| Preservative (benzoyl alcohol) | 0.9% by weight of total composition |

One drop (about 0.2 ml) of the composition was found to decrease pain and burning and decrease erythema of the inflammation associated therewith.

The term "topically applying" as used herein includes the application of the pharmacologically active ingredient to the surface being treated and the impregnation of the surface with the active ingredient.

What is claimed is:

1. Method for the relief of any one or more sensations of burning, pain and itching of the cutaneous or mucosal surface of animals and humans that is free of lesions comprising the step of topically applying to the situs of said condition a composition consisting essentially of (A) a compound selected from the group consisting of: (1) aminocaproic acid, (2) a compound of the formula $4NH_2CH_2(CH_2)_4COOH \cdot CaX_2$ wherein X is chloride or bromide, or (3) mixtures thereof, and (B) an inert pharmaceutically acceptable carrier, wherein said compound is present in an amount effective to diminish the sensations of burning, pain and itching.

2. The method of claim 1 wherein said compound is epsilon-aminocaproic acid.

3. The method of claim 2 comprising applying from 0.1 to 0.6 ml of said composition to said surface.

* * * * *